US00PP34692P2

(12) United States Plant Patent
Hansen

(10) Patent No.: US PP34,692 P2
(45) Date of Patent: Oct. 25, 2022

(54) **X *MANGAVE* PLANT NAMED 'BLACK MAGIC'**

(50) Latin Name: ***Manfreda* x *Agave***
Varietal Denomination: Black Magic

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 83 days.

(21) Appl. No.: 17/300,649

(22) Filed: Sep. 8, 2021

(51) Int. Cl.
*A01H 6/12* (2018.01)
*A01H 5/12* (2018.01)

(52) U.S. Cl.
USPC ..... Plt./373

(58) Field of Classification Search
USPC ..... Plt./373
CPC ..... A01H 6/12; A01H 5/12
See application file for complete search history.

*Primary Examiner* — Keith O. Robinson

(57) ABSTRACT

A new and unique X *Mangave* plant named 'Black Magic' characterized by compact habit of lanceolate foliage with near-black color in strong ultraviolet light exposure. The new plant has numerous bronze flowers on dense, tall, stiff, highly-branched scapes. The foliage has small, flexible, marginal teeth and flexible to semi-flexible terminal mucro. The new plant is suitable as a potted houseplant plant, as a container plant for the patio or garden and for the garden or planted in the landscape, and the flowers are loaded with nectar for attracting hummingbirds.

3 Drawing Sheets

Botanical classification: x *Manfreda* x *Agave* hybrid.
Variety denomination: 'Black Magic'.

STATEMENT REGARDING PRIOR DISCLOSURES UNDER 37 CFR 1.77(b)(6)

The first non-enabling public disclosure of x *Mangave* 'Black Magic' was on Mar. 2, 2020 as a brief description and photo on two websites operated by Walters Gardens, Inc. followed by the "Walters Gardens 2020-2021 Catalog" released on May 20, 2021. The first enabling disclosure of the new plant was a sale by Walters Gardens, Inc. to The Growing Place on Mar. 1, 2021. No plants were in condition to sell prior to this initial sale. Information for this website, catalog and plants for this sale were obtained from the inventor. No plants of x *Mangave* 'Black Magic' have been sold, in this country or anywhere in the world, nor has any disclosure of the new plant been made, more than one year prior the filing date of this application, and such disclosure within one year was either derived directly or indirectly from the inventor.

BACKGROUND OF THE INVENTION

The present invention relates to the new and distinct x *Mangave* plant, x *Mangave* 'Black Magic' hybridized on Nov. 20, 2015 by the inventor at a wholesale perennial nursery in Zeeland, Mich., USA as a cross between x *Mangave* 'Moonglow' U.S. Plant Pat. No. 29,195 as the female or seed parent and an unreleased proprietary hybrid x *Mangave* known by the breeder code 12-11-2 as the male or pollen parent. Through trials at the same nursery the plant was referred to by the code 16-36-7. The new plant has been successfully asexually propagated initially by division of offsets in 2019 followed by shoot tip tissue culture at the same nursery in Zeeland, Mich. These asexual propagation systems has been found to produce stable and identical plants that maintain all the unique characteristics of the original plant in successive generations.

BRIEF SUMMARY OF THE INVENTION

X *Mangave* 'Black Magic' differs from its parents as well as all other *Manfreda, Agave* and x *Mangave* known to the applicant. The most similar known x *Mangave* cultivars known to the inventor are: 'Coffee Jitters' U.S. Plant Pat. No. 31,275, 'Fiercely Fabulous' U.S. Plant Pat. No. 33,166, 'Silver Fox' U.S. Plant Pat. No. 29,642, 'Mayan Queen' U.S. Plant Pat. No. 31,312, 'Catch a Wave' U.S. Plant Pat. No. 29,723, 'Desert Dragon' U.S. Plant Pat. No. 31,311, 'Inkblot' U.S. Plant Pat. No. 29,431, and 'Night Owl' U.S. Plant patent application Ser. No. 17/300,222.

'Coffee Jitters' has narrower leaves that are coffee-colored, more twisted and more furrowed. 'Fiercely Fabulous' has broader leaves that are more upright in habit, or gray-green color with burgundy spotting and larger teeth. 'Silver Fox' has a similar habit but the foliage is wider, more glaucous with smoky-purple color and purple-lavender spots on the upper surface. 'Mayan Queen' has a wider more glaucous leaf surface with lighter grey-purple spotting. 'Catch a Wave' has leaves that are broader and more silvery-blue coloration and the leaves are more wavy and folded. 'Desert Dragon' has narrower and longer leaves with less greyed-purple spotting and more green, a more undulating margin and lack the large marginal teeth. 'Inkblot' has a more arching habit with longer foliage that is less intensely spotted and displays smaller marginal teeth. 'Night Owl' has broader foliage with a more glaucous surface, more developed marginal teeth and a lighter greyed-purple color.

The female parent, 'Moonglow', has narrower leaves with smaller teeth, and the habit is flatter. The male plant has wider leaves and is a larger plant and the leaves are more spotted and not a dark.

The new plant, 'Black Magic', is unique from all of these *Agave*, X *Mangave* and *Manfreda* known to the inventor by the following combined traits:

1. Compact mounded habit with 60 to 75 leaves at flowering;
2. Leaves lanceolate and nearly black in high light exposure;
3. Foliage with small flexible to semi-flexible marginal teeth and flexible to semi-flexible sharp apical mucro;
4. Moderate to rapid growth rate;
5. Numerous bronze flowers on dense, stiff, tall, highly-branched scapes.

BRIEF DESCRIPTION OF THE DRAWINGS

The photograph of the new plant demonstrates the overall appearance of the new plant including the unique traits as a three-year-old plant grown in a full-sun trial garden with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
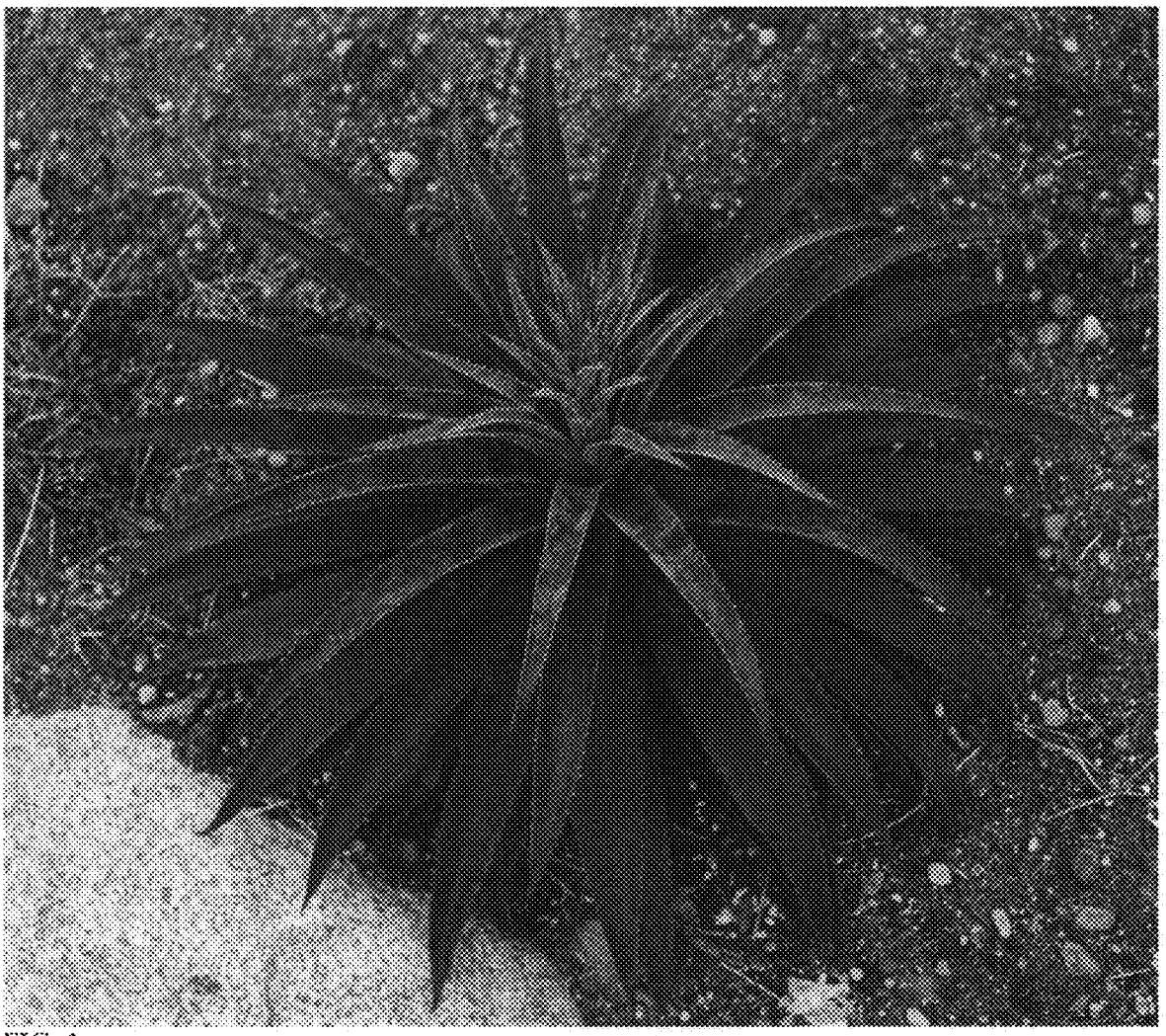
FIG. 1 shows the new plant from above with developing scape.
Figure 2:
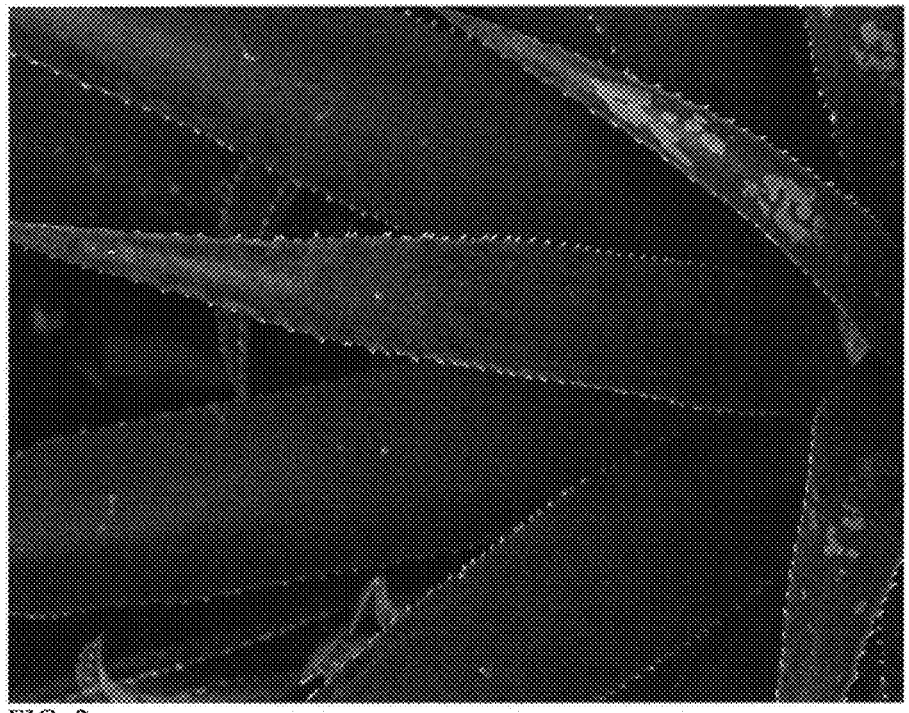
FIG. 2 shows a close-up of the foliage and marginal teeth.
Figure 3:
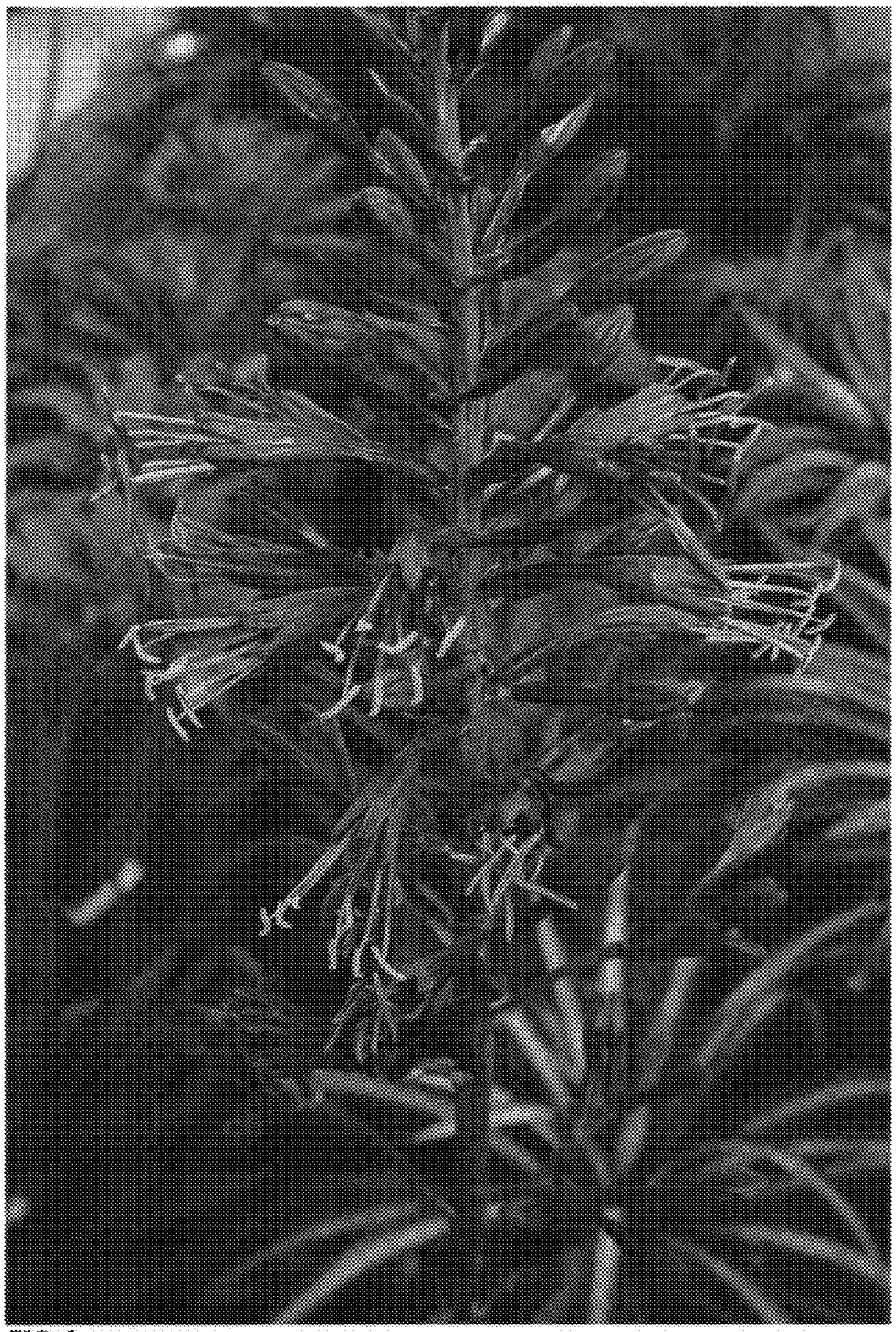
FIG. 3 shows a close-up of the flowers and buds in the upper scape.

The following descriptions and color references are based on the 2015 edition of The Royal Horticultural Society Colour Chart except where common dictionary terms are used. The new plant, X *Mangave* 'Black Magic', has not been observed under all possible environments. The phenotype may vary slightly with different environmental conditions, such as temperature, light, fertility, moisture and maturity levels, but without any change in the genotype. The following observations and size descriptions are of two and three-year old plants in a commercial wholesale greenhouse and also in a full-sun trial garden in Zeeland, Mich. with supplemental water and fertilizer as needed.

Botanical classification: x *Mangave* hybrid (*Manfreda* x *Agave*);

Parentage: 'Moonglow' as the female or seed parent and 12-11-2 as the male or pollen parent;

Propagation: Division and sterile plant tissue culture;

Time to initiate roots from tissue culture: About 21 days;

Growth rate: Moderate to rapid;

Crop time: About 12 to 16 weeks to finish during lengthening spring days from an established 25 mm tissue culture plug to a 65 mm diameter container;

Rooting habit: Fleshy, lightly branching, with roots up to 30 cm long;

Root color: Nearest RHS 158C depending on soil type;

Plant shape and habit: Succulent herbaceous perennial with basal rosettes of up to about 76 fleshy leaves radially emerging and arching from central rhizome, producing a symmetrical, low, rounded mound;

Plant size: Foliage height about 19.0 cm tall from soil line to the top of the leaves and 60.0 cm wide at soil level, scape to about 140.0 cm tall and flowering in upper about 66.0 cm tall and 20.0 cm wide at the widest flowers;

Foliage description: Lanceolate; simple; sarcous; fibrous; glabrous, slightly asperous and glaucous adaxial and abaxial; margins finely dentate with flexible teeth; apex acute with sharp flexible to semi-flexible mucro; base truncate, sessile, clasping; not sinuate; slightly concavo-convex and slightly arching with maturity;

Leaf size: To about 35.0 cm long, about 3.8 cm wide about one-third away from base, 3.5 cm wide at base, 0.8 cm thick and 1.5 cm deep; average about 31.5 cm long, 3.5 cm wide about one-third away from base, 3.0 cm wide at base and 1.0 cm thick; typically bi-laterally symmetrical; spots of variable sizes from about 1.5 mm diameter to about 13.0 mm long and 8.0 mm across, frequently overlapping; teeth to about 1.0 mm long and 1.0 mm across at base;

Foliage fragrance: None observed;

Cauline bracts: About 16 per scape below flowers and one at each branch; lanceolate; simple; sarcous, glabrous; margins finely dentate with flexible teeth to about 0.5 mm long; apex narrowly acute with semi-flexible mucro to about 3.5 mm long; base truncate, sessile, clasping; typically adpressed in proximal two-thirds; to about 13.5 cm long and about 1.9 cm wide near base, decreasing distally;

Leaf blade and bract color:

*Adaxial* (*young*).—Nearest RHS N187B with spots nearest RHS N186B.

*Abaxial* (*young*).—Nearest RHS 191B with spots nearest RHS 187B.

*Adaxial* (*mature*).—Blend nearest RHS N187C, with spots of nearest RHS N187A.

*Abaxial* (*mature*).—Nearest RHS 137B near longitudinal center and nearest and RHS N186A at edges.

*Marginal teeth*.—Adaxial and abaxial apical portion nearest RHS 157D; adaxial and abaxial proximal portion nearest RHS 185B.

Mucro: Flexible to semi-flexible; sharp; straight, about 5.0 mm long and 1.0 mm across;

Mucro color: Nearest RHS 165A;

Petiole: Sessile;

Veins: Parallel; not distinct;

Peduncle: Terete; glaucous; glabrous; stiff; strong; upwardly; heavily branched with about 21 branches; about 140.0 cm long and to 1.2 cm diameter at base and 2.0 cm diameter below first branches; branches to about 10.0 cm long and about 0.4 cm diameter at base; branch aspect upwardly and outwardly distally becoming more outwardly, about 30 degrees from horizontal;

Peduncle color: Proximally between RHS N186B and RHS N187A, distally nearest RHS 147B finely and lightly maculate with anthocyanin nearest RHS 187A; branches between RHS N186B and RHS N187A;

Pedicel: Typically absent, rarely to about 2.0 mm long and 3.0 mm diameter; terete; glaucous; glabrous; stiff; strong;

Pedicel color: When present nearest RHS 147B;

Buds one day prior to opening: Elongated globose; about 5.0 cm long and about 9.0 mm across at bulb, base about 5.0 mm diameter, bulb about 2.6 cm long;

Bud color: Dorsally nearest RHS 137A and heavily maculate with nearest RHS N186B, ventrally nearest RHS 146B;

Flower description: Perfect; incomplete; actinomorphic; about 8.0 cm long to exserted anthers and pistil and opening to about 3.07 cm across at outside of anthers; corolla to about 5.9 cm long and 1.8 cm wide at apex; lasting about 3 to 4 days per flower; flowering period about three weeks once plant is mature, approximately three-years-old; producing abundant nectar;

Inflorescence: Approximately 100 to 150 flowers per scape; aspect mostly upright; flowering portion about 66.0 cm tall and about 20.0 cm across;

Flower fragrance: None detected;

Tepals: Six in two sets of three; lanceolate; glabrous and lustrous adaxial and abaxial; outer set acute apex, about 30.0 mm long, fused in basal 17.0 mm, free in distal 13.0 mm and about 5.0 mm wide just above fusion; inner set rounded apex, fused in basal 17.0 mm, free in distal 13.0 mm, about 30.0 mm long and 4.0 mm wide just above fusion, inner set creased on abaxial side along margin where overlapped with outer set while in bud;

Tepal color: Outer tepal set adaxial basal one-third nearest RHS 145D, middle portion nearest RHS 145B, distal one-third between RHS 187A and RHS 187B; outer set abaxial nearest RHS 137A with moderate anthocyanins spotting of nearest RHS N186B; inner tepal set adaxial basal one-third nearest RHS 145D, middle portion nearest RHS 145B, distal one-third between RHS 187A and RHS 187B; abaxial inner set base nearest RHS 137A with moderate anthocyanins spotting of nearest RHS N186B with 1.0 mm wide margin in free portion nearest RHS 160B proximally and strongly blushed to solid RHS 187B toward apex;

Androecium: Six;

*Filaments*.—Six; terete distally, slightly applanate base; stiff and straight; about 52.0 mm long and 2.0 mm across at base; adnate with inner corolla in proximal 12.0 mm; color nearest RHS 145C proximally and distally nearest RHS 162D moderately maculate with nearest RHS 183D.

*Anther*.—Dorsifixed; longitudinal; straight, oblong; about 19.0 mm long and 2.5 mm diameter before opening; color nearest blend between RHS 174B and RHS 174A.

*Pollen*.—Abundant; color nearest RHS 8B.

Gynoecium: Single; 54.0 mm long;

*Style*.—50.0 mm long and 1.5 mm diameter at base; color at base nearest RHS 145C, distally between RHS 146C and RHS 145C and heavily maculate in the middle portion with nearest RHS 187C.

*Stigma*.—Turbinate, apex tri-lobed; distally puberulent; about 2.0 mm tall and 3.0 mm across top; color side nearest RHS 177A; top stigmatic surface in tri-pointed star with color nearest RHS 155D.

*Ovary*.—Inferior; oblong; about 19.0 mm long and 5.0 mm across; surface smooth; color nearest RHS 146D.

Fruit: Not yet observed;

Seed: Not yet observed;

Disease resistance: x *Mangave* 'Black Magic' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'Black Magic' as herein described and illustrated.

* * * * *